(12) United States Patent
Quick et al.

(10) Patent No.: US 11,433,218 B2
(45) Date of Patent: Sep. 6, 2022

(54) CATHETER SHAFT AND ASSOCIATED DEVICES, SYSTEMS, AND METHODS

(71) Applicant: Inari Medical, Inc., Irvine, CA (US)

(72) Inventors: Richard Quick, Mission Viejo, CA (US); Brian J. Cox, Laguna Niguel, CA (US)

(73) Assignee: Inari Medical, Inc., Irvine, CA (US)

( * ) Notice: Subject to any disclaimer, the term of this patent is extended or adjusted under 35 U.S.C. 154(b) by 39 days.

(21) Appl. No.: 16/062,877

(22) PCT Filed: Dec. 19, 2016

(86) PCT No.: PCT/US2016/067628
§ 371 (c)(1),
(2) Date: Jun. 15, 2018

(87) PCT Pub. No.: WO2017/106877
PCT Pub. Date: Jun. 22, 2017

(65) Prior Publication Data
US 2018/0361116 A1 Dec. 20, 2018

Related U.S. Application Data

(60) Provisional application No. 62/269,372, filed on Dec. 18, 2015.

(51) Int. Cl.
*A61M 25/00* (2006.01)
(52) U.S. Cl.
CPC ..... *A61M 25/0045* (2013.01); *A61M 25/0054* (2013.01); *A61M 2025/0059* (2013.01)

(58) Field of Classification Search
CPC .......... A61M 25/0045; A61M 25/0054; A61M 2025/0059
USPC ....................................................... 604/523
See application file for complete search history.

(56) References Cited

U.S. PATENT DOCUMENTS

| 2,846,179 A | 8/1958 | Monckton |
| 3,088,363 A | 5/1963 | Sparks |
| 3,197,173 A | 7/1965 | Taubenheim |
| 3,435,826 A | 4/1969 | Fogarty |

(Continued)

FOREIGN PATENT DOCUMENTS

| CN | 103932756 | 7/2014 |
| JP | 6190049 | 7/1994 |

(Continued)

OTHER PUBLICATIONS

International Search Report and Written Opinion for International App. No. PCT/US2015/034987, dated Jun. 9, 2015, 12 pages.

(Continued)

*Primary Examiner* — Phillip A Gray
(74) *Attorney, Agent, or Firm* — Perkins Coie LLP

(57) ABSTRACT

Catheter shafts and associated devices, systems, and methods are disclosed herein, A representative catheter in accordance with an embodiment of the disclosure includes a generally tubular outer structure and an inner structure surrounded by the outer structure. The inner structure surrounds a catheter lumen. The inner structure includes overlapping edges such that, when the catheter is bent along its longitudinal axis, the over-lapping edges move relative to one another.

17 Claims, 5 Drawing Sheets

(56) References Cited

U.S. PATENT DOCUMENTS

| | | |
|---|---|---|
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,287,808 A | 9/1981 | Leonard et al. |
| 4,393,872 A | 7/1983 | Reznik et al. |
| 4,523,738 A | 6/1985 | Raftis et al. |
| 4,551,862 A | 11/1985 | Haber |
| 4,650,466 A | 3/1987 | Luther |
| 4,873,978 A | 10/1989 | Ginsburg |
| 4,883,458 A | 11/1989 | Shiber |
| 4,890,611 A | 1/1990 | Monfort et al. |
| 4,960,259 A | 10/1990 | Sunnanvader et al. |
| 4,978,341 A | 12/1990 | Niederhauser |
| 5,011,488 A | 4/1991 | Ginsburg |
| 5,059,178 A | 10/1991 | Ya |
| 5,102,415 A | 4/1992 | Guenther et al. |
| 5,127,626 A | 7/1992 | Hilal et al. |
| 5,129,910 A | 7/1992 | Phan et al. |
| 5,192,286 A | 3/1993 | Phan et al. |
| 5,192,290 A | 3/1993 | Hilal |
| 5,360,417 A | 11/1994 | Gravener et al. |
| 5,370,653 A | 12/1994 | Cragg |
| 5,476,450 A | 12/1995 | Ruggio |
| 5,490,859 A | 2/1996 | Mische et al. |
| 5,591,137 A | 1/1997 | Stevens |
| 5,746,758 A | 5/1998 | Nordgren et al. |
| 5,749,858 A | 5/1998 | Cramer |
| 5,766,191 A | 6/1998 | Trerotola |
| 5,782,817 A | 7/1998 | Franzel et al. |
| 5,827,229 A | 10/1998 | Auth et al. |
| 5,827,304 A | 10/1998 | Hart |
| 5,868,708 A | 2/1999 | Hart et al. |
| 5,873,866 A | 2/1999 | Kondo et al. |
| 5,873,882 A | 2/1999 | Straub et al. |
| 5,876,414 A | 3/1999 | Straub |
| 5,882,329 A | 3/1999 | Patterson et al. |
| 5,911,710 A | 6/1999 | Barry et al. |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,066,149 A | 5/2000 | Samson et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,254,571 B1 | 7/2001 | Hart |
| 6,258,115 B1 | 7/2001 | Dubrul |
| 6,306,163 B1 | 10/2001 | Fitz |
| 6,350,271 B1 | 2/2002 | Kurz et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,413,235 B1 | 7/2002 | Parodi |
| 6,423,032 B2 | 7/2002 | Parodi |
| 6,440,148 B1 | 8/2002 | Shiber |
| 6,454,741 B1 | 9/2002 | Muni et al. |
| 6,454,775 B1 | 9/2002 | Demarais et al. |
| 6,458,103 B1 | 10/2002 | Albert et al. |
| 6,458,139 B1 | 10/2002 | Palmer et al. |
| 6,511,492 B1 | 1/2003 | Rosenbluth et al. |
| 6,514,273 B1 | 2/2003 | Voss et al. |
| 6,530,935 B2 | 3/2003 | Wensel et al. |
| 6,530,939 B1 | 3/2003 | Hopkins et al. |
| 6,544,279 B1 | 4/2003 | Hopkins et al. |
| 6,551,342 B1 | 4/2003 | Shen et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,605,074 B2 | 8/2003 | Zadno-Azizi et al. |
| 6,605,102 B1 | 8/2003 | Mazzocchi et al. |
| 6,623,460 B1 | 9/2003 | Heck |
| 6,635,070 B2 | 10/2003 | Leeflang et al. |
| 6,645,222 B1 | 11/2003 | Parodi et al. |
| 6,660,013 B2 | 12/2003 | Rabiner et al. |
| 6,663,650 B2 | 12/2003 | Sepetka et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,755,847 B2 | 6/2004 | Eskuri |
| 6,767,353 B1 | 7/2004 | Shiber |
| 6,800,080 B1 | 10/2004 | Bates |
| 6,824,553 B1 | 11/2004 | Gene et al. |
| 6,939,361 B1 | 9/2005 | Kleshinski |
| 6,960,222 B2 | 11/2005 | Vo et al. |
| 7,004,954 B1 | 2/2006 | Voss et al. |
| 7,036,707 B2 | 5/2006 | Aota et al. |
| 7,041,084 B2 | 5/2006 | Fojtik |
| 7,052,500 B2 | 5/2006 | Bashir et al. |
| 7,056,328 B2 | 6/2006 | Arnott |
| 7,069,835 B2 | 7/2006 | Nishri et al. |
| 7,094,249 B1 | 8/2006 | Thomas et al. |
| 7,179,273 B1 | 2/2007 | Palmer et al. |
| 7,220,269 B1 | 5/2007 | Ansel et al. |
| 7,232,432 B2 | 6/2007 | Fulton, III et al. |
| 7,244,243 B2 | 7/2007 | Lary |
| 7,285,126 B2 | 10/2007 | Sepetka et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,534,234 B2 | 5/2009 | Fojtik |
| 7,578,830 B2 | 8/2009 | Kusleika et al. |
| 7,621,870 B2 | 11/2009 | Berrada et al. |
| 7,674,247 B2 | 3/2010 | Fojtik |
| 7,691,121 B2 | 4/2010 | Rosenbluth et al. |
| 7,695,458 B2 | 4/2010 | Belley et al. |
| 7,763,010 B2 | 7/2010 | Evans et al. |
| 7,766,934 B2 | 8/2010 | Pal et al. |
| 7,775,501 B2 | 8/2010 | Kees |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fojtik |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,088,140 B2 | 1/2012 | Ferrera et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fojtik |
| RE43,902 E | 1/2013 | Hopkins et al. |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,486,105 B2 | 7/2013 | Demond et al. |
| 8,491,539 B2 | 7/2013 | Fojtik |
| 8,512,352 B2 | 8/2013 | Martin |
| 8,535,334 B2 | 9/2013 | Martin |
| 8,545,526 B2 | 10/2013 | Martin et al. |
| 8,568,432 B2 | 10/2013 | Straub |
| 8,574,262 B2 | 11/2013 | Ferrera et al. |
| 8,579,915 B2 | 11/2013 | French et al. |
| 8,585,713 B2 | 11/2013 | Ferrera et al. |
| 8,696,622 B2 | 4/2014 | Fiorella et al. |
| 8,715,314 B1 | 5/2014 | Janardhan et al. |
| 8,771,289 B2 | 7/2014 | Mohiuddin et al. |
| 8,777,893 B2 | 7/2014 | Malewicz |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |

(56) References Cited

U.S. PATENT DOCUMENTS

| | | |
|---|---|---|
| 8,795,345 B2 | 8/2014 | Grandfield et al. |
| 8,801,748 B2 | 8/2014 | Martin |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,845,621 B2 | 9/2014 | Fojtik |
| 8,852,205 B2 | 10/2014 | Brady et al. |
| 8,852,226 B2 | 10/2014 | Gilson et al. |
| 8,932,319 B2 | 1/2015 | Martin et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 8,992,504 B2 | 3/2015 | Castella et al. |
| 9,005,172 B2 | 4/2015 | Chung |
| 9,101,382 B2 | 8/2015 | Krolik et al. |
| 9,149,609 B2 | 10/2015 | Ansel et al. |
| 9,161,766 B2 | 10/2015 | Slee et al. |
| 9,204,887 B2 | 12/2015 | Cully et al. |
| 9,259,237 B2 | 2/2016 | Quick et al. |
| 9,283,066 B2 | 3/2016 | Hopkins et al. |
| 9,408,620 B2 | 8/2016 | Rosenbluth |
| 9,439,664 B2 | 9/2016 | Sos |
| 9,439,751 B2 | 9/2016 | White et al. |
| 9,456,834 B2 | 10/2016 | Folk |
| 9,463,036 B2 | 10/2016 | Brady et al. |
| 9,526,864 B2 | 12/2016 | Quick |
| 9,526,865 B2 | 12/2016 | Quick |
| 9,566,424 B2 | 2/2017 | Pessin |
| 9,579,116 B1 | 2/2017 | Nguyen et al. |
| 9,616,213 B2 | 4/2017 | Furnish et al. |
| 9,636,206 B2 | 5/2017 | Nguyen et al. |
| 9,700,332 B2 | 7/2017 | Marchand et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,844,386 B2 | 12/2017 | Nguyen et al. |
| 9,844,387 B2 | 12/2017 | Marchand et al. |
| 9,999,493 B2 | 6/2018 | Nguyen et al. |
| 10,004,531 B2 | 6/2018 | Rosenbluth et al. |
| 10,045,790 B2 | 8/2018 | Cox et al. |
| 10,098,651 B2 | 10/2018 | Marchand et al. |
| 10,226,263 B2 | 3/2019 | Look et al. |
| 10,335,186 B2 | 7/2019 | Rosenbluth et al. |
| 10,342,571 B2 | 7/2019 | Marchand et al. |
| 10,349,960 B2 | 7/2019 | Quick |
| 10,524,811 B2 | 1/2020 | Marchand et al. |
| 10,588,655 B2 | 3/2020 | Rosenbluth et al. |
| 10,912,577 B2 | 2/2021 | Marchand et al. |
| 11,058,445 B2 | 7/2021 | Cox et al. |
| 11,058,451 B2 | 7/2021 | Marchand et al. |
| 11,147,571 B2 | 10/2021 | Cox et al. |
| 11,154,314 B2 | 10/2021 | Quick |
| 2001/0004699 A1 | 6/2001 | Gittings et al. |
| 2001/0041909 A1 | 11/2001 | Tsugita et al. |
| 2001/0051810 A1 | 12/2001 | Dubrul et al. |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0156457 A1 | 10/2002 | Fisher |
| 2002/0161392 A1 | 10/2002 | Dubrul |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135230 A1 | 7/2003 | Massey et al. |
| 2003/0153973 A1 | 8/2003 | Soun et al. |
| 2004/0039412 A1 | 2/2004 | Isshiki et al. |
| 2004/0073243 A1 | 4/2004 | Sepetka et al. |
| 2004/0138692 A1 | 7/2004 | Phung et al. |
| 2004/0199202 A1 | 10/2004 | Dubrul et al. |
| 2005/0038468 A1 | 2/2005 | Panetta et al. |
| 2005/0119668 A1 | 6/2005 | Teague et al. |
| 2005/0283165 A1 | 12/2005 | Gadberry |
| 2005/0283186 A1 | 12/2005 | Berrada et al. |
| 2006/0047286 A1 | 3/2006 | West |
| 2006/0100662 A1 | 5/2006 | Daniel et al. |
| 2006/0247500 A1 | 11/2006 | Voegele et al. |
| 2006/0253145 A1 | 11/2006 | Lucas |
| 2006/0282111 A1 | 12/2006 | Morsi |
| 2007/0038225 A1 | 2/2007 | Osborne |
| 2007/0112374 A1 | 5/2007 | Paul, Jr. et al. |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0255252 A1 | 11/2007 | Mehta |
| 2008/0015541 A1 | 1/2008 | Rosenbluth et al. |
| 2008/0088055 A1 | 4/2008 | Ross |
| 2008/0157017 A1 | 7/2008 | Macatangay et al. |
| 2008/0167678 A1 | 7/2008 | Morsi |
| 2008/0228209 A1 | 9/2008 | DeMello et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0300466 A1 | 12/2008 | Gresham |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0281525 A1 | 11/2009 | Harding et al. |
| 2009/0292307 A1 | 11/2009 | Razack |
| 2010/0087850 A1 | 4/2010 | Razack |
| 2010/0114113 A1 | 5/2010 | Dubrul et al. |
| 2010/0121312 A1 | 5/2010 | Gielenz et al. |
| 2010/0204712 A1 | 8/2010 | Mallaby |
| 2010/0249815 A1 | 9/2010 | Jantzen et al. |
| 2010/0318178 A1 | 12/2010 | Rapaport et al. |
| 2011/0054405 A1 | 3/2011 | Whiting et al. |
| 2011/0060212 A1 | 3/2011 | Slee et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1* | 10/2011 | Sakata .............. A61M 25/0013 |
| | | 604/526 |
| 2011/0251629 A1 | 10/2011 | Galdonik et al. |
| 2011/0264133 A1 | 10/2011 | Hanlon et al. |
| 2011/0319917 A1 | 12/2011 | David et al. |
| 2012/0059356 A1 | 3/2012 | di Palma et al. |
| 2012/0089216 A1 | 4/2012 | Rapaport et al. |
| 2012/0101480 A1* | 4/2012 | Ingle .................... B29C 53/821 |
| | | 156/190 |
| 2012/0101510 A1 | 4/2012 | Lenker et al. |
| 2012/0138832 A1 | 6/2012 | Townsend |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0232655 A1 | 9/2012 | Lorrison et al. |
| 2012/0271231 A1 | 10/2012 | Agrawal |
| 2012/0310166 A1 | 12/2012 | Huff |
| 2013/0030460 A1 | 1/2013 | Marks et al. |
| 2013/0092012 A1 | 4/2013 | Marchand et al. |
| 2013/0102996 A1 | 4/2013 | Strauss |
| 2013/0184703 A1 | 7/2013 | Brice et al. |
| 2013/0289608 A1 | 10/2013 | Tanaka et al. |
| 2014/0005713 A1 | 1/2014 | Bowman |
| 2014/0025048 A1 | 1/2014 | Ward |
| 2014/0155830 A1 | 6/2014 | Bonnette et al. |
| 2014/0276403 A1 | 9/2014 | Follmer et al. |

(56) References Cited

U.S. PATENT DOCUMENTS

| | | |
|---|---|---|
| 2014/0371779 A1 | 12/2014 | Vale et al. |
| 2015/0018860 A1 | 1/2015 | Quick et al. |
| 2015/0025555 A1 | 1/2015 | Sos |
| 2015/0032144 A1 | 1/2015 | Holloway |
| 2015/0059908 A1* | 3/2015 | Mollen ............... B32B 1/08 138/132 |
| 2015/0133990 A1 | 5/2015 | Davidson |
| 2015/0196744 A1 | 7/2015 | Aboytes |
| 2015/0238207 A1 | 8/2015 | Cox et al. |
| 2015/0265299 A1 | 9/2015 | Cooper et al. |
| 2015/0305756 A1 | 10/2015 | Rosenbluth et al. |
| 2015/0305859 A1 | 10/2015 | Eller |
| 2015/0352325 A1 | 12/2015 | Quick |
| 2015/0360001 A1 | 12/2015 | Quick |
| 2015/0374391 A1 | 12/2015 | Quick et al. |
| 2016/0113666 A1 | 4/2016 | Quick et al. |
| 2016/0143721 A1 | 5/2016 | Rosenbluth et al. |
| 2016/0206344 A1 | 7/2016 | Bruzzi et al. |
| 2016/0262790 A1 | 9/2016 | Rosenbluth et al. |
| 2016/0277276 A1 | 10/2016 | Cox et al. |
| 2017/0014560 A1 | 1/2017 | Minskoff et al. |
| 2017/0037548 A1 | 2/2017 | Lee |
| 2017/0058623 A1 | 3/2017 | Jaffrey et al. |
| 2017/0105745 A1 | 4/2017 | Rosenbluth et al. |
| 2017/0112514 A1 | 4/2017 | Marchand et al. |
| 2017/0189041 A1 | 7/2017 | Cox et al. |
| 2017/0233908 A1 | 8/2017 | Kroczynski et al. |
| 2017/0265878 A1 | 9/2017 | Marchand et al. |
| 2017/0325839 A1 | 11/2017 | Rosenbluth et al. |
| 2018/0064453 A1 | 3/2018 | Garrison et al. |
| 2018/0064454 A1 | 3/2018 | Losordo et al. |
| 2018/0092652 A1 | 4/2018 | Marchand et al. |
| 2018/0105963 A1 | 4/2018 | Quick |
| 2018/0125512 A1 | 5/2018 | Nguyen et al. |
| 2018/0193043 A1 | 7/2018 | Marchand et al. |
| 2018/0256178 A1 | 9/2018 | Cox et al. |
| 2018/0296240 A1 | 10/2018 | Rosenbluth et al. |
| 2018/0344339 A1 | 12/2018 | Cox et al. |
| 2019/0000492 A1 | 1/2019 | Casey et al. |
| 2019/0070401 A1 | 3/2019 | Merritt et al. |
| 2019/0150959 A1 | 5/2019 | Cox et al. |
| 2019/0231373 A1 | 8/2019 | Quick |
| 2019/0321071 A1 | 10/2019 | Marchand et al. |
| 2020/0046368 A1 | 2/2020 | Merritt et al. |
| 2021/0113224 A1 | 4/2021 | Dinh |
| 2021/0186541 A1 | 6/2021 | Thress |
| 2021/0290925 A1 | 9/2021 | Merritt et al. |
| 2021/0330344 A1 | 10/2021 | Rosenbluth et al. |
| 2021/0378694 A1 | 12/2021 | Thress et al. |
| 2022/0000505 A1 | 1/2022 | Hauser |
| 2022/0000506 A1 | 1/2022 | Hauser |
| 2022/0000507 A1 | 1/2022 | Hauser |

FOREIGN PATENT DOCUMENTS

| | | |
|---|---|---|
| JP | H07323090 A | 12/1995 |
| JP | 2001522631 | 5/1999 |
| JP | 2004097807 A | 4/2004 |
| JP | 2005230132 A | 9/2005 |
| JP | 2005323702 A | 11/2005 |
| JP | 2006094876 A | 4/2006 |
| JP | 2011526820 | 1/2010 |
| WO | WO-1997017889 A1 | 5/1997 |
| WO | WO-1999044542 | 9/1999 |
| WO | WO-2000053120 | 9/2000 |
| WO | WO2004018916 | 3/2004 |
| WO | WO-2005046736 | 5/2005 |
| WO | WO-2006110186 | 10/2006 |
| WO | WO-2007092820 A2 | 8/2007 |
| WO | WO2009082513 | 7/2009 |
| WO | WO-20091 55571 A1 | 12/2009 |
| WO | WO-2009155571 A1 | 12/2009 |
| WO | WO2010002549 | 1/2010 |
| WO | WO-2010010545 A1 | 1/2010 |
| WO | WO-201 0023671 A2 | 3/2010 |
| WO | WO-2010023671 A2 | 3/2010 |
| WO | WO-201 0049121 A2 | 5/2010 |
| WO | WO-2010049121 A2 | 5/2010 |
| WO | WO-201 0102307 A1 | 9/2010 |
| WO | WO-2010102307 A1 | 9/2010 |
| WO | WO2011032712 | 3/2011 |
| WO | WO-2011054531 A2 | 5/2011 |
| WO | WO-2012009675 A2 | 1/2012 |
| WO | WO-201 2011097 | 4/2012 |
| WO | WO-2012011097 | 4/2012 |
| WO | WO-201 2/065748 A1 | 5/2012 |
| WO | WO-2012/065748 A1 | 5/2012 |
| WO | WO2012120490 | 9/2012 |
| WO | WO-2014047650 A1 | 3/2014 |
| WO | WO-2014081892 A1 | 5/2014 |
| WO | WO-2015006782 A1 | 1/2015 |
| WO | WO-2015061365 A1 | 4/2015 |
| WO | WO2015121424 | 8/2015 |
| WO | WO2015191646 | 12/2015 |
| WO | WO2017024258 | 2/2017 |
| WO | WQ2017024258 | 2/2017 |
| WO | WO2017070702 | 4/2017 |
| WO | WQ2017070702 | 4/2017 |
| WO | WO2017106877 | 6/2017 |
| WO | WO2018080590 | 5/2018 |
| WO | WQ2018080590 | 5/2018 |
| WO | WO2018148174 | 8/2018 |
| WO | WO2019050765 | 3/2019 |
| WO | WO2019075444 | 4/2019 |
| WO | WO2020036809 | 2/2020 |
| WO | WO2021248042 | 12/2021 |

OTHER PUBLICATIONS

International Search Report and Written Opinion for International Application No. PCT/US2015/034987, dated Sep. 17, 2015, 12 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", CardiologyRounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al., "Massive pulmonary embolism: review of management strategies with a focus on catheter- based techniques", Expert Rev. Cardiovasc. Ther. 8(6), 863-873 (2010).

Liu, S. et al., "Massive Pulmonary Embolism: Treatment with the Rotarex Thrombectomy System", Cardiovascular Interventional Radiology; 2011: 34:106-113.

(56) References Cited

OTHER PUBLICATIONS

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Notice of Allowance for U.S. Appl. No. 13/843,742, dated Mar. 12, 2014, 13 pages.
Notice of Allowance for U.S. Appl. No. 14/288,778, dated Dec. 23, 2014, 12 pages.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T, et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "Adapt Fast study: a direct aspiration first pass technique for acute stroke thrombectomy." J NeuroIntervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Raiology*, Oct. 2006, 41, 729-734.
International Search Report and Written Opinion for International App. No. PCT/US2015/034987 filed Jun. 9, 2015, Applicant: Inceptus Medical, LLC, dated Sep. 17, 2015, 12 pages.
English translation of Japanese Office Action received for JP Application No. 2016-564210, Applicant: Inceptus Medical, LLC, dated Sep. 4, 2017, 4 pages.
Australian Exam Report received for AU Application No. 2015274704, Applicant: Inceptus Medical, LLC, dated Sep. 7, 2017, 3 pages.
European Search Report received for EP Application No. 15805810.7, Applicant: Inceptus Medical, LLC, dated Sep. 4, 2017, 6 pages.
International Search Report and Written Opinion for International App. No. PCT/US2016/067628 filed Dec. 19, 2016, Applicant: Inari Medical, Inc, dated Apr. 10, 2017, 11 pages.
International Search Report and Written Opinion for International App. No. PCT/US2017/029696, dated Apr. 26, 2017, Applicant: Inari Medical, Inc, dated Sep. 15, 2017, 19 pages.
International Search Report and Written Opinion for International App. No. PCT/US2016/058536, Date of Filing: Oct. 24, 2016, Applicant: Inari Medical, Inc, dated Mar. 13, 2017, 14 pages.
European Patent Application No. 13838945.7, Extended European Search Report, 9 pages, Apr. 15, 2016.
Gibbs, et al., "Temporary Stent as a bail-out device during percutaneous transluminal coronary angioplasty: preliminary clinical experience," British Heart Journal, 1994, 71:372-377, Oct. 12, 1993 6 pgs.
Goldhaber, S. et al. "Percutaneous Mechanical Thrombectomy for Acute Pulmonary Embolism—A Double-Edged Sword", American College of CHEST Physicians, Aug. 2007: 132:2, 363-372.
Goldhaber, S., "Advanced treatment strategies for acute pulmonary embolism, including thrombolysis and embolectomy", Journal of Thrombosis and Haemostasis, 2009: 7 (Suppl. 1): 322-327.
Gupta, S. et al., "Acute Pulmonary Embolism Advances in Treatment," JAPI, Association of Physicians India, Mar. 2008, vol. 56, 185-191.
International Search Report and Written Opinion for International App. No. PCT/US13/61470, dated Jan. 17, 2014, 7 pages.
International Search Report and Written Opinion for International App. No. PCT/US2014/046567, dated Nov. 3, 2014, 13 pages.
International Search Report and Written Opinion for International App. No. PCT/US2014/061645, dated Jan. 23, 2015, 15 pages.
International Search Report and Written Opinion for International App. No. PCT/US2017/029696, Date of Filing: Apr. 26, 2017, Applicant: Inari Medical, Inc, dated Sep. 15, 2017, 19 pages.
European First Office Action received for EP Application No. 13838945.7, Applicant: Inari Medical, Inc., dated Oct. 26, 2018, 7 pages.
International Search Report and Written Opinion for International App. No. PCT/US2018/048786, Date of Filing: Aug. 30, 2018, Applicant: Inari Medical, Inc., dated Dec. 13, 2018, 12 pages.
International Search Report and Written Opinion for International App. No. PCT/US2018/055780, Date of Filing: Oct. 13, 2018, Applicant: Inceptus Medical LLC., dated Jan. 22, 2019, 8 pages.
European Search Report for European Application No. 16876941.2, Date of Filing: Dec. 19, 2016, Applicant: Inari Medical, Inc., dated Jul. 18, 2019, 7 pages.
Extended European Search Report for European Application No. 16858462.1, Date of Filing: Oct. 24, 2016, Applicant: Inari Medical, Inc., dated Jun. 3, 2019, 10 pages.
International Search Report and Written Opinion for International App. No. PCT/US2019/045794, Date of Filing: Aug. 8, 2019, Applicant: Inari Medical, Inc., dated Nov. 1, 2019, 17 pages.
Partial Supplementary European Search Report for European Application No. 17864818.4, Date of Filing: May 21, 2019, Applicant: Inari Medical, Inc., dated Apr. 24, 2020, 12 pages.
International Search Report and Written Opinion for International App. No. PCT/US2020/056067, Date of Filing: Oct. 16, 2020; Applicant: Inari Medical, Inc., dated Jan. 22, 2021, 8 pages.
Extended European Search Report for European Application No. 20191581.6, Applicant: Inari Medical, Inc., dated Mar. 31, 2021, 11 pages.
International Search Report and Written Opinion for International App. No. PCT/US2020/055645, Date of Filing: Dec. 17, 2020; Applicant: Inari Medical, Inc., dated Apr. 14, 2021, 12 pages.
Extended European Search Report for European Application No. 18853465.5, Applicant: Inari Medical, Inc., dated May 7, 2021, 2021, 7 pages.
International Search Report and Written Opinion for International App. No. PCT/US21/35965, Date of Filing: Jun. 4, 2021, Applicant: Inari Medical, Inc., dated Sep. 28, 2021, 12 pages.
English translation of Japanese Office action dated May 2, 2022 for Japanese Application No. 2018-531067, 3 pages.

* cited by examiner

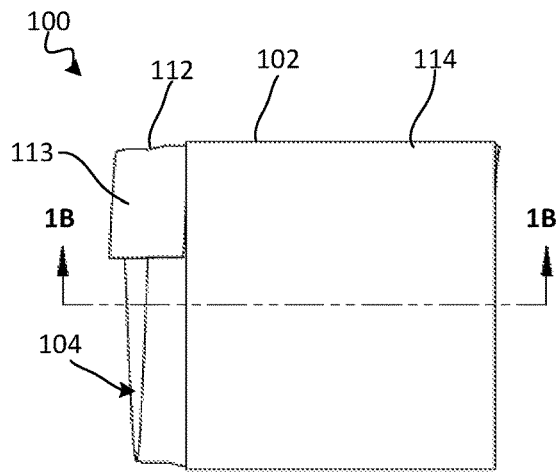
Figure 1A
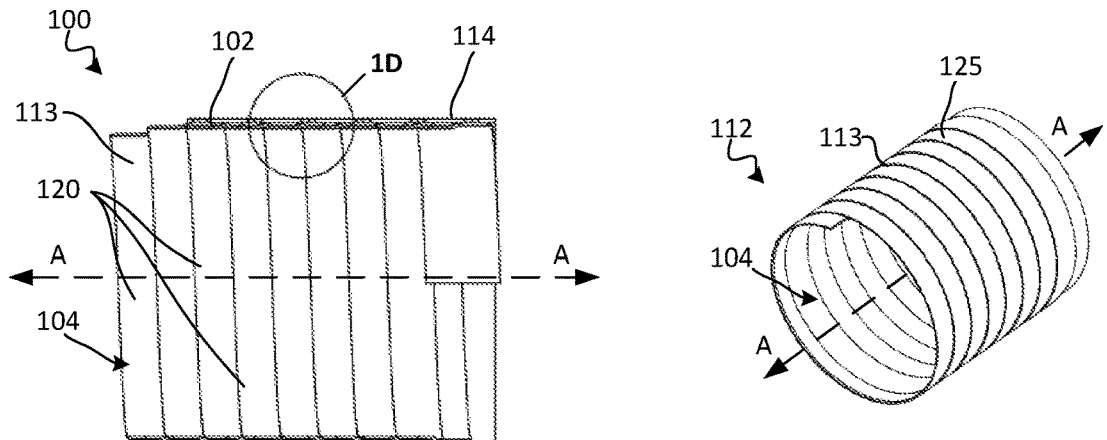
Figure 1B
Figure 1C
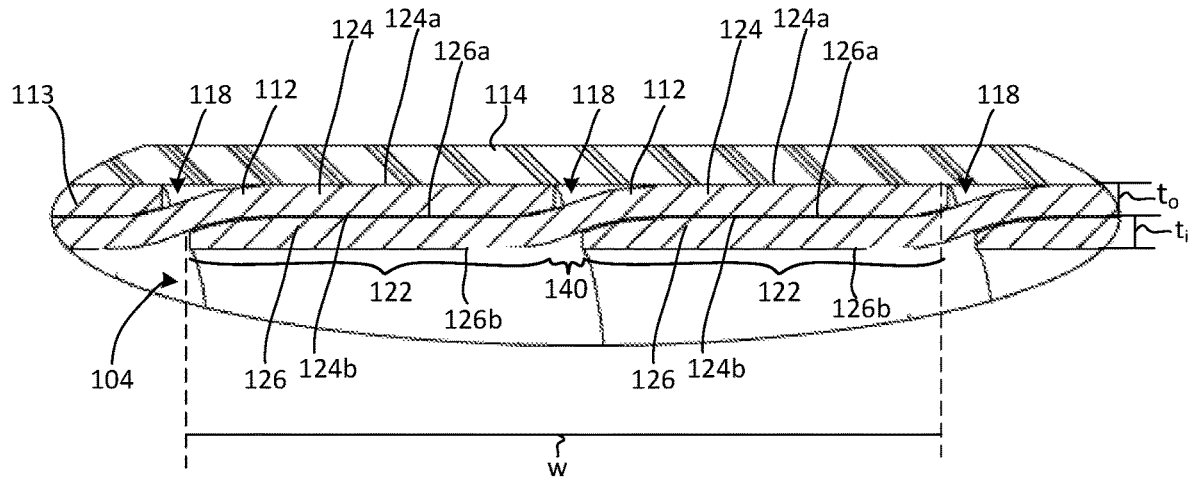
Figure 1D

CATHETER SHAFT AND ASSOCIATED DEVICES, SYSTEMS, AND METHODS

CROSS-REFERENCE TO RELATED APPLICATION(S)

This application is a 35 U.S.C. § National Phase application of International Patent Application No. PCT/US2016/067628, filed Dec. 19, 2016, which claims priority to U.S. Provisional Application No. 62/269,372, filed on Dec. 18, 2015, titled "CATHETER SHAFT AND ASSOCIATED DEVICES, SYSTEMS, AND METHODS," the contents of which are hereby incorporated by reference in their entireties.

TECHNICAL FIELD

The present technology is directed generally to catheters. More specifically, the present technology relates to catheter shaft construction.

BACKGROUND

A wide variety of medical devices have been developed for intravascular use. Catheters, for example, are commonly used to facilitate navigation through and/or treatment within the anatomy of a patient. Because of the compromises involved between the mechanical, biological and chemical requirements for catheter performance, many existing catheters are a composite of two or more different materials in order to take advantage of the unique properties of the different materials. For example, a common composite catheter construction includes (1) an outer jacket made of a material that provides longitudinal rigidity to resist, kinks and (2) a chemically-inert inner surface liner (typically a fluoropolymer) having a low coefficient of friction to ease delivery of one or more components through the shaft lumen. Inner liner materials, however, are significantly less flexible than the materials used for the outer jacket, and thus greatly affect the flexibility of the composite catheter shaft. For example, the modulus of elasticity of materials commonly used as inner surface liners is about 70,000 psi, while the modulus of elasticity for common outer jacket material(s) is about 2,900 psi. Although some conventional catheters are made with low durometer polymers, e.g., extremely soft), such catheters generally have little kink resistance. Accordingly, a need exists for a kink-resistant catheter shall with improved flexibility.

BRIEF DESCRIPTION OF THE DRAWINGS

FIG. 1A is a side view of a portion of a catheter shaft configured in accordance with the present technology, shown in an unstressed state.

FIG. 1B is a cross-sectional view of the catheter shaft shown in FIG. 1A, taken along line 1B-1B.

FIG. 1C is an isolated, isometric view of an inner structure of the catheter shaft shown in FIGS. 1A-1B configured in accordance with the present technology.

FIG. 1D is an enlarged view of a portion of the cross-sectioned catheter shall shown in FIG. 1B.

DETAILED DESCRIPTION

Figure 2A:
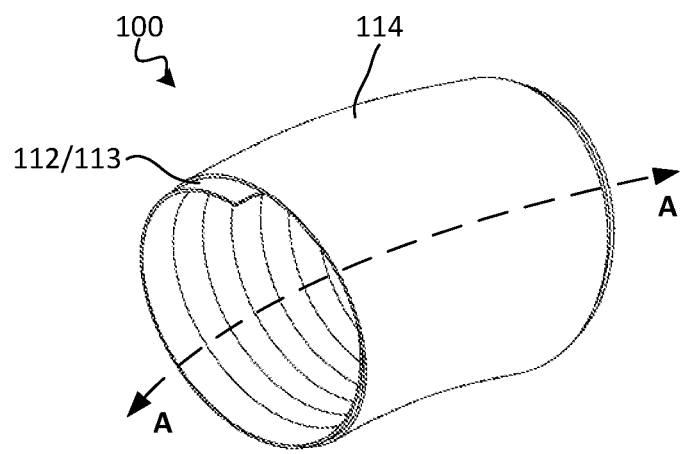
FIG. 2A is an isometric view of the catheter shaft shown in FIGS. 1A-1C, shown bent along a curved axis.

The present technology is directed to catheters and associated methods of manufacture. Specific details of several embodiments of catheter devices, systems, and methods in accordance with the present technology are described below with reference to FIGS. 1A-4C. In one embodiment, the present technology includes a catheter shaft composed of a tubular outer structure and a helical inner structure surrounded by the outer structure. The inner structure can be formed of a strip of material wound around a central longitudinal axis such that the edges of the strip overlap to form a continuous tubular wall. In some embodiments, only an exposed portion of the strip defines an exterior surface of the continuous tubular wall. The exposed portion can be bonded to the outer structure while a remaining portion of the strip remains free to slide relative to the exposed portion. Accordingly, the catheter shaft of the present technology is significantly more flexible than a comparable shaft utilizing an inner structure made of a contiguous tube.

I. SELECTED EMBODIMENTS OF CATHETER SHAFTS

FIGS. 1A and 1B are side and cross-sectional views, respectively, of a portion of a composite catheter shaft 100 (also referred to herein as "the shaft 100") configured in accordance with the present technology shown in an unstressed state. Referring to FIGS. 1A-1B together, the catheter shaft 100 includes a generally tubular sidewall 102 that defines a lumen 104 therethrough. The lumen 104 is configured to slidably receive and facilitate the passage therethrough of one or more medical devices, such as catheters, cannulas, access ports, guidewires, implants, infusion devices, stents and/or stem-grafts, intravascular occlusion devices, clot retrievers, stent retrievers, implantable heart valves, and other suitable medical devices and/or associated delivery systems. Additionally, the lumen 104 can be configured to receive one or more fluids therethrough, such as radiopaque dye, saline, drugs, and the like.

The size of the lumen 104 can vary depending on the desired characteristics of the shaft 100. For example, in some embodiments the shaft 100 can have an inner diameter (e.g., lumen diameter) between about 0.01 inches and about 0.5 inches, and in some embodiments between about 0.2 inches and about 0.4 inches. Although the shaft 100 shown in FIGS. 1A-1B has a generally round (e.g., circular) cross-sectional shape, it will be appreciated that the shaft 100 can include other cross-sectional shapes or combinations of shapes. For example, the cross-sectional shape of the shaft 100 can be oval, oblong, rectangular, square, triangular, polygonal, and/or any other suitable shape and/or combination of shapes.

As shown in FIGS. 1A-1B, the sidewall 102 of the shaft 100 includes an outer structure 114 and an inner structure 112 surrounded by the outer structure 114. An end portion of the outer structure 114 has been removed in FIGS. 1A-1B to better illustrate the structural features of the inner structure 112; generally, the outer structure 114 surrounds the inner structure 112 along the entire length of the inner structure 112. In some embodiments, the outer structure 114 can be an elongated polymer tube. Suitable materials for the outer structure 114 include Pebax® (poly ether block amide), polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PEA), polyether-ester, platinum, polymer/metal composites, etc., or mixtures, blends or combinations thereof.

FIG. 1C is an isolated isometric view of the inner structure 112 alone without the outer structure 114. As shown in FIGS. 1A-1C, the inner structure 112 can be a single strip 113 of material wound around a central longitudinal axis A such that the edges of the strip 113 overlap to form a continuous/contiguous (e.g., gap-free) tubular wall having a discontinuous exterior surface 125 in a longitudinal direction. The inner structure 112 and/or strip 113 can be made of a material having a low coefficient of friction, such as a fluoropolymer and/or a lubricious polymer (e.g., high density polyethylene (HDPE), polytetrafluoroethylene (PTFE), and/or a copolymer of tetrafluoroethylene with perfluoroethers such as perfluoroalkoxy (PEA), perfluoropropyl vinyl ether, and/or perfluoromethyl vinyl ether). Other suitable materials can include PEEK, PE, PP, or a copolymer of tetrafluoroethylene, FEP, etc. In many embodiments of the present technology, the inner structure material(s) has a higher melting point than the outer structure material(s).

As shown in the enlarged, cross-sectional view of the shaft 100 in FIG. 1D, the wound strip 113 has an overlapping region 122 that defines a subduction zone and a non-overlapping region 140. In the embodiment shown in FIGS. 1A-1D, a width of the overlapping region 122 is generally the same along the length of the shaft 100. In other embodiments, a width of the overlapping region 122 can vary along the length of the shaft 100. In a representative embodiment, when the shaft 100 is in an unstressed state, about 50% or less of the strip 113 covered. Such a configuration avoids gradually increasing a thickness of the inner structure 112 in a given longitudinal direction. In other embodiments, the percentage of overlap can be more than 50%. The amount of overlap (or pitch of a helical strip) may be varied along the length of the shaft to create regions of different and/or changing stiffness.

The overlapping region 122 includes an outer portion 124 of the strip 113 and an inner portion 126 of the strip 113 positioned radially inwardly of the outer portion 124, as shown in FIG. 1D. The outer portion 124, inner portion 126, and non-overlapping region 140 together define a width w of the strip 113. Additionally, a thickness of the inner structure 112 can be the sum of the thicknesses of the outer portion 124 and the inner portion 126 (labeled $t_o$ and $t_i$, respectively), or two times a thickness of the strip 113.

The outer portion 124 can have an outer surface 124a facing radially outwardly and an inner surface 124b opposite the outer surface 124a and facing the lumen 104. The inner portion 126 has an outer surface 126a facing radially outwardly and an inner surface 126b opposite the outer surface 126a and facing the lumen 104. In the embodiment shown in FIGS. 1A-1D, the outer surface 124a of the outer portion 124 is bonded or otherwise fixed to the outer structure 114 along all or a portion of the length of the outer portion 124. The shaft 100 can include a gap 118 between adjacent turns of the outer portion 124 and the outer structure 114. The inner surface 124b of the outer portion 124 abuts the outer surface 126a of the inner portion 126 along all or a portion of their respective lengths. Because the strip 113 is made of a material having a low coefficient of friction, the inner surface 124b of the outer portion 124 can contact the outer surface 126a of the inner portion 126, yet retain the ability to slide relative to the outer surface 126a (and vice versa) when the shaft 100 is bent along its axis A. Additionally, the inner surface 126b of the inner portion 126 can define the shaft lumen 104, as shown in FIG. 1D.

Figure 2B:
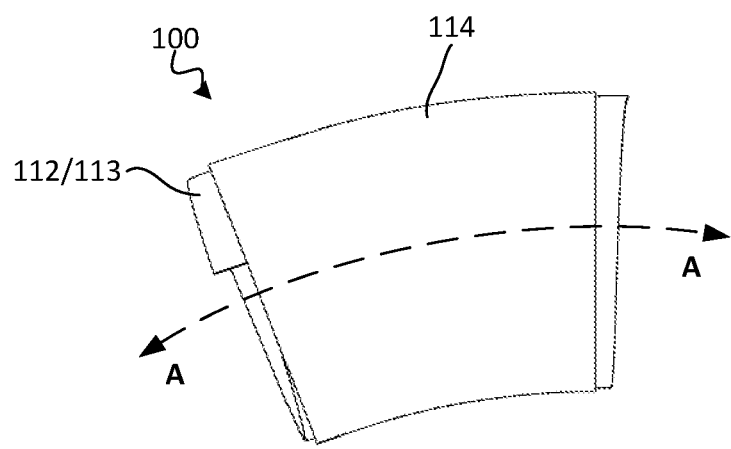
FIG. 2B is a side view of the catheter shaft shown in FIG. 2A.
Figure 2C:
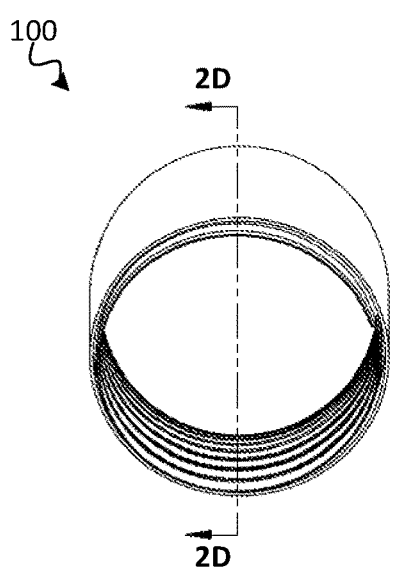
FIG. 2C is an isometric front view of the catheter shaft shown in FIGS. 2A and 2B.
Figure 2D:
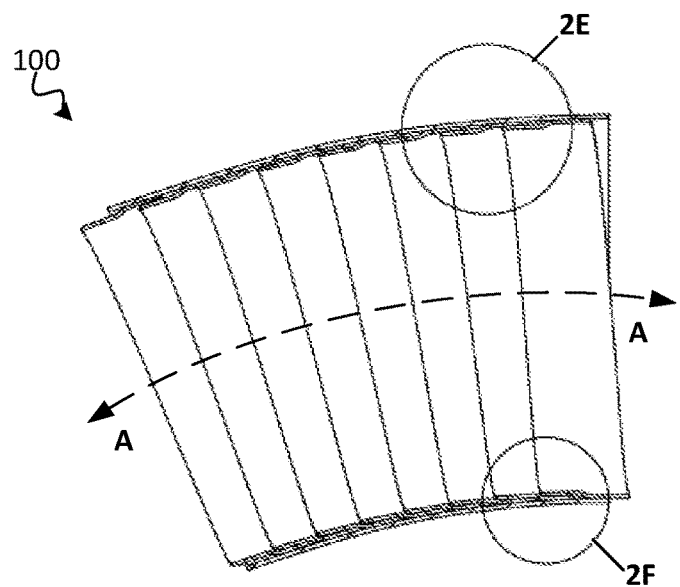
FIG. 2D is a cross-sectional view of the catheter shaft shown in FIGS. 2A-2C taken along line 2D-2D of the view shown in FIG. 2C.
Figure 2E:
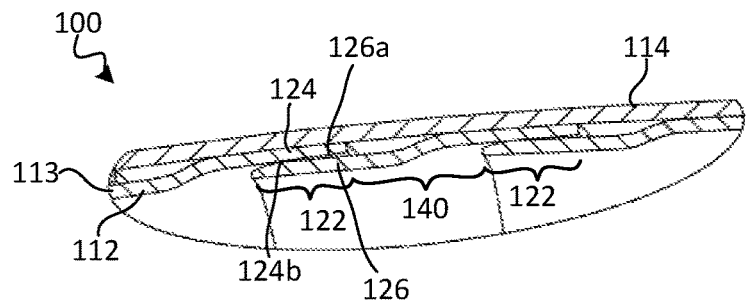
FIG. 2E is an enlarged view of a portion of the cross-sectioned catheter shaft shown in FIG. 2D.
Figure 2F:
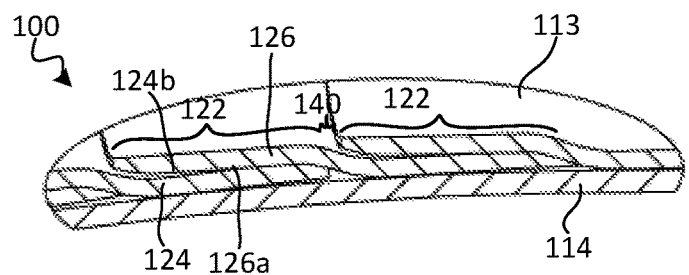
FIG. 2F is an enlarged view of a portion of the cross-sectioned catheter shaft shown in FIG. 2D.

FIGS. 2A-2C are an isometric view, a side view, and an isometric front view, respectively, of the catheter shaft 100 in accordance with the present technology, shown bent along axis A (e.g., a curved axis upon bending). FIG. 2D is a cross-sectional view of the catheter shaft shown in FIGS. 2A-2C taken along line 2D-2D of the view shown in FIG. 2C, and FIGS. 2E and 2F are enlarged views of a portion of the cross-sectioned catheter shaft 100 shown in FIG. 2D. Referring to FIGS. 2A-2F together, when the shaft 100 bends or deforms, the outer structure 114 deforms elastically and threes the fixed outer portion 124 to move and bend with it. As the outer portion 124 moves, the inner portion 126 slides along the inner surface 124b of the outer portion 124. Along portions of the shaft 100 experiencing tensile forces, the width of the overlapping region 122 decreases, as shown in FIG. 2E. Along portions of the shaft 100 experiencing compressive forces, the width of the over-lapping region 122 increases, as shown in FIG. 2F, as the outer portion 124 subducts with respect to the inner portion 126.

The catheter shaft 100 of the present technology provides several advantages over existing catheters. For example, the helical or spiral geometry of the inner structure 112, as well as the inner structure's 112 interrupted bonding with the outer structure 114, greatly increases the overall flexibility of the inner structure 112 as compared to a continuous tube made of the same material and having the same thickness. As such, the catheter shaft 100 of the present technology is significantly more flexible than conventional catheter shafts. For example, in some embodiments, the bending stiffness of the shaft 100 may be 25% less than that of a comparable composite catheter shaft (e.g., a shaft having the same outer structure and an inner structure made of a continuous tube made of the same material, having the same thickness and the same inner diameter). In some embodiments, the bending stiffness may be between about 30% and about 60% less than that of a comparable composite catheter. In some embodiments, the inner structure may provide less than about 50%, and in other embodiments less than about 25%, of the total bending stiffness of the composite catheter. Such improved flexibility is most dramatic in larger diameter catheters (assuming wall thickness does not vary based on diameter), such as guide catheters. For a given bend radius and wall thickness, the walls of catheters with a large ID are subject to greater strain than the walls of small ID catheters.

II. SELECTED METHODS OF MANUFACTURE

In one embodiment of manufacturing a catheter shaft in accordance with the present technology, a strip of material is provided. In some embodiments, the strip can be made of the desired inner structure material, such as PTFE. The strip can be a PTFE tape, a longitudinally-cut PTFE tube (described in greater detail below), or other polymer structures in a strip form. For example, in some embodiments, the strip is constructed by splitting the wall of a polymer tube along a helical path about the tube's longitudinal axis. In any of the foregoing embodiments, the strip of material may be wound around a mandrel. In a representative embodiment, the strip is wound from the proximal end to the distal end such that the strips' free edges or steps face distally within the lumen. The strip can be wound in this manner to provide a smoother path through the lumen for one or more devices delivered therethrough. In other embodiments, the strip can be wound from its distal end to its proximal end.

The strip can be wound to have a desired pitch angle (e.g., the distance between successive turns of the strip). The pitch angle affects the flexibility of the resulting wound structure since the pitch angle affects the amount of overlapping regions per unit length of the shaft, which in turn affects the width of bonded strip that (eventually) undergoes bending stress. In some embodiments, the maximum pitch angle to achieve 50% coverage can be governed by the equation max pitch angle=$\tan^{-1}(2\pi D/w)$, and the minimum pitch angle to achieve no overlap can be governed by the equation min pitch angle=$\tan^{-1}(\pi D/w)$, where D is the desired inner diameter for the shaft and w is the width of the strip of material.

Once the strip is wound around the mandrel as desired, a tube of material (e.g., a polymer commonly used for the outer structure) is positioned over the wound strip. Next, a heat-shrinkable tube (e.g., a fluoropolymer) can be positioned over the tube. The assembly (e.g., the mandrel, the wound strip, the tube, and the heat-shrinkable tube) is then gradually heated from its distal end to its proximal end (or vice versa) to fuse the tube with the strip. The amount of calories absorbed by the assembly, and the rate at which the calories are transferred to the mandrel, will depend on the geometry of the assembly (e.g., the length of the assembly, the diameter of the assembly, the thickness of the materials used, etc.). The temperature can be high enough to shrink the heat-shrinkable tube and raise the temperature of the tube material above its glass transition temperature (e.g., between about 380° F. and about 440° F.), yet low enough so as not to affect the durometer of the tube material and affect its resultant molecular weight (thereby charging the mechanical properties of the resultant outer structure). Also, the duration of heat application can be monitored to avoid for applying too high of a temperature for too long, which may cause the tube material to flow between the overlapping portion of the strip and into the lumen thereby raising the coefficient of friction within the catheter lumen. Additionally, the mandrel material can be chosen to provide a heatsink to quickly remove heat from the melted tube and freeze it before the tube material flows between the overlaps. For example, in some embodiments the mandrel is a steel tube, and the wall thickness of the tube can be varied to add or subtract heat transfer rate. Once the assembly has cooled, the heat shrinkable tube can be removed and the newly-formed composite shaft can be removed from the mandrel.

In any of the devices and methods disclosed herein, the inner structure is formed of a polymer tube (e.g., a PTFE tube) that is cut into strips in a direction parallel to the longitudinal axis of the tube. The width of the strip is then ($\pi D$) where D is the tubing diameter. The thickness of the strip is the wall thickness of the tubing. Another method of creating strip from tubing is to slice the tube helically. The maximum width of the strip is then ($\pi D$)/(tan θ), where θ is the angle of the helix from the tube axis.

Before cutting the tube, the tube can be etched on only its exterior surface to increase the coefficient of friction between the exterior surface of the tube and other polymers (i.e., the outer structure material) that may be bonded to the exterior surface of the tube. The tubing may be etched with a strong base (e.g., sodium hydroxide, potassium hydroxide, sodium/ammonia, etc.) by immersing the tube in liquid etchant as an on-line process during extrusion, or as a batch process after extrusion. The latter method includes plugging the ends of the PTFE tubing before immersion or otherwise keeping the open ends out of the liquid etchant. This way, only one surface of the polymer tubing material is etched while the other surface is not etched.

III. ADDITIONAL EMBODIMENTS

Figure 3A:
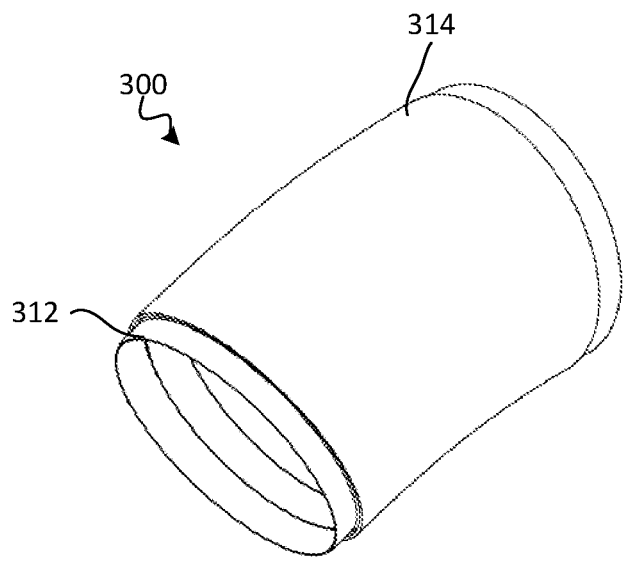
FIG. 3A is an isometric view of a catheter shaft configured in accordance with another embodiment of the present technology, shown bent along its axis.
Figure 3B:
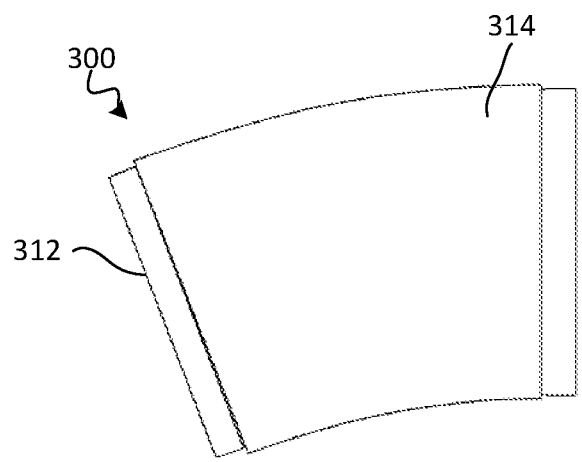
FIG. 3B is a side view of the catheter shaft shown in FIG. 3A.
Figure 4A:
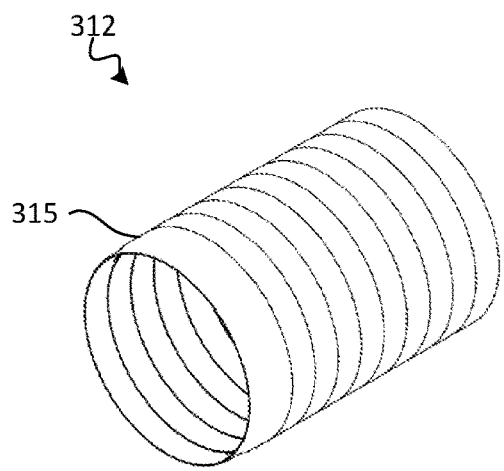
FIG. 4A is an isolated, isometric view of an inner structure of the catheter shaft shown in FIGS. 3A-3B configured in accordance with the present technology, shown in an unstressed state.
Figure 4B:
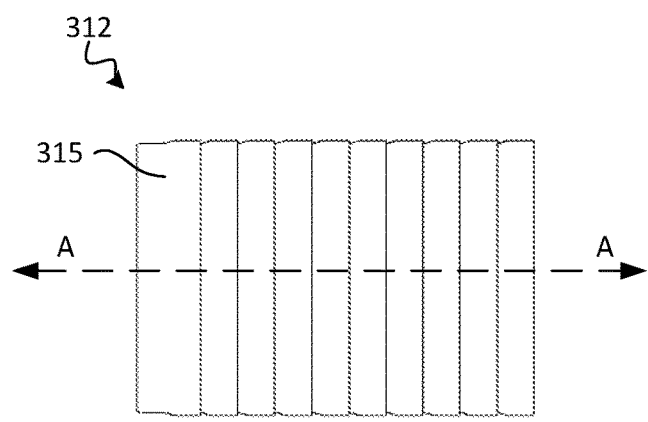
FIG. 4B is an isolated side view of the inner structure shown in FIG. 4A.
Figure 4C:
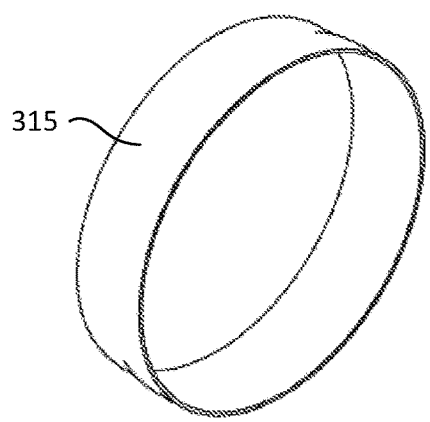
FIG. 4C is an isolated segment of the inner structure shown in FIGS. 4A-4B configured in accordance with the present technology.

FIGS. 3A and 3B are isometric and side views, respectively, of a catheter shaft 300 (also referred to herein as "the shaft 300") configured in accordance with another embodiment of the present technology, shown bent along its axis A. As shown in FIGS. 3A and 3B, the shaft 300 can include an outer structure 314 and an inner structure 312 surrounded by the outer structure 314. FIGS. 4A and 4B are side and isometric views of the inner structure 312 isolated from the shaft 300. In the embodiment shown in FIGS. 3A-4B, the inner structure 312 is formed of a plurality of overlapping segments 315, such as rings. An isolated segment 315 is shown in FIG. 4C. The segments 315 can have a generally cylindrical or conical shape. Additionally, referring to FIG. 4B, individual segments 315 can have an outer portion 326 having an inner diameter and an inner portion 326 having an outer diameter that fits within the inner diameter of the outer portion 326. The segments 315 can be arranged as shown in FIG. 4B such that the inner portion 326 of one segment 315 is received within the outer portion 324 of an immediately adjacent segment 315. The inner portions 326 accordingly overlap the outer portions 324 in a manner similar to the embodiments described above with respect to FIGS. 1A-2F. The outer portions 326 are fixed to the outer structure 314, but inner portions 326 can slide over the inner surface of the outer portions 326. As a result, the shaft 300 is expected to have similar advantages to those described above with respect to the shaft 100.

IV. EXAMPLES

The following examples are illustrative of several embodiments of the present technology:

1. A catheter, comprising:
a generally tubular outer structure; and
an inner structure surrounded by the outer structure and that surrounds a catheter lumen.

2. The catheter of example 1, wherein the inner structure includes over-lapping edges.

3. The catheter of example 1 or example 2, wherein the inner structure is non-continuous in a longitudinal direction.

4. The catheter of any one of examples 1-3, wherein the inner structure has freely sliding interfaces with itself.

5. The catheter of any one of examples 1-4, wherein the inner structure provides less than 50% of the total bending stiffness of the catheter.

6. The catheter of any one of examples 1-5, wherein the inner structure has portions that slide tangentially during bending of the catheter.

7. A catheter, comprising
a generally tubular outer structure, the outer structure having an outer surface and an inner surface; and
an inner structure surrounded by the outer structure, the inner structure having a relaxed state and a stressed state, and wherein
the inner structure is composed of a strip of material that is helically wound around a central longitudinal axis to form a generally tubular member defining a lumen, wherein the strip has an outer surface and an inner surface,
a first portion of the strip overlaps a second portion of the strip along the longitudinal axis of the strip,
only a portion of the outer surface is bonded to the inner surface of the outer structure, and
when the catheter is bent along its longitudinal axis, the second portion is configured to slide relative to the first portion.

8. The catheter of example 7, wherein the inner structure includes over-lapping edges.

9. The catheter of example 7 or example 8, wherein the inner structure is non-continuous in a longitudinal direction.

10. The catheter of any one of examples 7-9, wherein the inner structure provides less than 50% of the total bending stiffness of the catheter.

11. The catheter of any one of examples 7-10, wherein the first portion slides tangentially relative to the second portion during bending of the catheter.

12. The catheter of any one of examples 7-11, wherein the strip of material is formed from a polymer tube that has been cut in a direction parallel to a longitudinal axis of the tube.

13. the catheter of any one of examples 7-11, wherein the strip of material is formed from a polymer tube that has been cut in a helical direction.

14. The catheter of any one of examples 7-13, wherein the polymer tube has an etched exterior surface and an inner surface that is not etched.

14. The catheter of any one of examples 7-13, wherein the polymer tube is a PTFE tube.

V. CONCLUSION

Many embodiments of the present technology can be used to access or treat targets located in tortuous and narrow vessels, such as certain sites in the neurovascular system, the pulmonary vascular system, the coronary vascular system, and/or the peripheral vascular system. The catheter shaft of the present technology can also be suited for use in the digestive system, soft tissues, and/or any other insertion into an organism for medical uses.

It will be appreciated that specific elements, substructures, advantages, uses, and/or other features of the embodiments described with reference to FIGS. 1A-4C can be suitably interchanged, substituted or otherwise configured with one another in accordance with additional embodiments of the present technology. For example, a single catheter shaft can include an inner structure having a helical portion (as shown in FIGS. 1A-2F) and a segmented portion (as shown in FIGS. 3A-4C). A person of ordinary skill in the art, therefore, will accordingly understand that the technology can have other embodiments with additional elements, or the technology can have other embodiments without several of the features shown and described above with reference to FIGS. 1A-4C. For example, the catheters of the present technology can be used with any of the clot treatment devices and associated devices, systems, and methods disclosed in U.S. patent application Ser. No. 14/299,933, filed Jun. 9, 2014, and U.S. patent application Ser. No. 13/843, 742, filed Mar. 15, 2013, and U.S. patent application Ser. No. 14/735,110, filed Jun. 9, 2015, all of which are incorporated herein by reference in their entireties. Additionally, in some embodiments, the catheter shaft of the present technology can include additional structures and/or layers. For example, in a particular embodiment, the shaft includes an additional structure or material positioned between the inner structure and the outer structure. Moreover, in a particular embodiment, the shaft includes more than one strip.

We claim:

1. A catheter, comprising:
a generally tubular outer structure; and
an inner structure surrounded by the outer structure and that surrounds a catheter lumen, wherein the inner structure extends along a longitudinal axis and includes over-lapping edges that overlap in a radial direction relative to the longitudinal axis, wherein the overlapping edges extend entirely circumferentially about the longitudinal axis, and wherein the over-lapping edges are not adhered together.

2. A catheter, comprising:
a generally tubular outer structure; and
an inner structure surrounded by the outer structure, wherein the inner structure is non-continuous in a longitudinal direction, wherein the inner structure has a freely sliding interface with itself in a radial direction relative to the longitudinal axis, and wherein the freely sliding interface extends entirely circumferentially about the longitudinal axis.

3. A catheter, comprising:
a generally tubular outer structure; and
an inner structure surrounded by the outer structure, wherein the inner structure extends along a longitudinal axis, wherein the inner structure has freely sliding interfaces with itself in a radial direction relative to the longitudinal axis, and wherein the freely sliding interfaces extend entirely circumferentially about the longitudinal axis.

4. A catheter, comprising:
a generally tubular outer structure; and
an innermost structure surrounded by the outer structure, wherein the innermost structure extends along a longitudinal axis, wherein the innermost structure provides less than 50% of the total bending stiffness of the catheter, wherein the inner structure has a freely sliding interface with itself in a radial direction relative to the longitudinal axis, and wherein the freely sliding interface extends entirely circumferentially about the longitudinal axis.

5. A catheter, comprising a generally tubular outer structure; and
an inner structure surrounded by the outer structure, wherein the inner structure extends along a longitudinal axis, wherein the inner structure has inner portions and outer portions that overlap in a radial direction relative to the longitudinal axis, wherein the inner portions and the outer portions overlap entirely circumferentially about the longitudinal axis, and wherein the inner portions are configured to slide tangentially relative to the outer portions during bending of the catheter.

6. A catheter, comprising a generally tubular outer structure, the outer structure having an outer surface and an inner surface; and
an inner structure surrounded by the outer structure, wherein the inner structure is composed of a strip of material that is helically wound around a central longitudinal axis to form a generally tubular member defining a lumen, wherein the strip has an outer surface and an inner surface, wherein the strip is wound to have an overlapping region at which a first portion of the strip overlaps a second portion of the strip in a radial direction relative to the longitudinal axis of the strip, and wherein, at the overlapping region of the strip
the outer surface of the first portion of the strip is at least partially bonded to the inner surface of the outer structure, and
the outer surface of the first portion of the strip (a) faces the inner surface of the second portion of the strip and (b) is configured to slide relative to the inner surface of the first portion of the strip when the inner structure is bent relative to the longitudinal axis.

7. The catheter of claim 3, wherein
the outer structure has an outer surface and an inner surface; and
the inner structure has a relaxed state and a stressed state, and wherein
the inner structure is composed of a strip of material that is helically wound around the longitudinal axis to form a generally tubular member defining a lumen, wherein the strip has an outer surface and an inner surface,
a first portion of the strip overlaps a second portion of the strip along the longitudinal axis,
only a portion of the outer surface of the inner structure is bonded to the inner surface of the outer structure, and
when the inner structure is bent along the longitudinal axis, the second portion is configured to slide relative to the first portion.

8. The catheter of claim 3 wherein the inner structure includes over-lapping edges.

9. The catheter of claim 3 wherein the over-lapping edges are not bonded together.

10. The catheter of claim 3 wherein the inner structure does not include an adhesive between the over-lapping edges.

11. The catheter of claim 3 wherein the inner structure is composed of a strip of material that is helically wound around the longitudinal axis to form a generally tubular member defining a lumen.

12. The catheter of claim 11 wherein the strip of material is formed from a polymer tube that has been cut in a direction parallel to a longitudinal axis of the tube.

13. The catheter of claim 11 wherein the strip of material is formed from a polymer tube that has been cut in a helical direction.

14. The catheter of claim 11 wherein the strip of material is formed from a polymer tube that has an etched exterior surface and an inner surface that is not etched.

15. The catheter of claim 11 wherein the strip of material is formed from a PTFE tube.

16. The catheter of claim 3 wherein the outer structure as an inner surface, wherein the inner structure has an outer surface, and wherein only a portion the outer surface of the inner structure is bonded to the inner surface of the outer structure.

17. The catheter of claim 6 wherein the overlapping region extends entirely circumferentially about the longitudinal axis.

* * * * *